US012766077B2

(12) United States Patent
Sacchetti et al.

(10) Patent No.: US 12,766,077 B2
(45) Date of Patent: Oct. 20, 2026

(54) ENTERAL FEEDING PUMP SYSTEMS, VALVE ASSEMBLIES THEREFOR AND FLUID FLOW CONTROL METHODS FOR SAME

(71) Applicant: AMSINO MEDICAL INC., Shanghai (CN)

(72) Inventors: Peter J. Sacchetti, North Falmouth, MA (US); Carlo Ruggeri, Lincoln, RI (US)

(73) Assignee: AMSINO MEDICAL INC., Shanghai (CN)

(*) Notice: Subject to any disclaimer, the term of this patent is extended or adjusted under 35 U.S.C. 154(b) by 166 days.

(21) Appl. No.: 18/649,791

(22) Filed: Apr. 29, 2024

(65) Prior Publication Data

US 2024/0358601 A1 Oct. 31, 2024

Related U.S. Application Data

(63) Continuation of application No. 18/325,985, filed on May 30, 2023, now Pat. No. 11,992,464, which is a (Continued)

(51) Int. Cl.
*A61M 39/28* (2006.01)
*A61J 15/00* (2006.01)
(Continued)

(52) U.S. Cl.
CPC ....... *A61J 15/0092* (2013.01); *A61J 15/0076* (2015.05); *A61M 39/227* (2013.01);
(Continued)

(58) Field of Classification Search
CPC .. A61M 39/28; A61M 39/228; A61M 5/1407; A61M 39/22; A61M 39/223; A61M 5/16827; A61J 15/0076; A61J 15/0092
See application file for complete search history.

(56) References Cited

U.S. PATENT DOCUMENTS 3,411,534 A 11/1968 Rose
4,061,142 A 12/1977 Tuttle
(Continued)

FOREIGN PATENT DOCUMENTS

CN 110327218 A 10/2019
EP 1604699 A2 * 12/2005 .......... A61M 1/1607
(Continued)

OTHER PUBLICATIONS

"International Search Report and Written Opinion received for PCT Patent Application No. PCT/US2022/075110, mailed on Jan. 17, 2023", 11 pages.
(Continued)

*Primary Examiner* — Nilay J Shah
(74) *Attorney, Agent, or Firm* — Getech Law LLC; Jun Ye

(57) ABSTRACT

A flow selector valve assembly for an enteral feeding pump system (i.e., an enteral feeding pump system including a fluid delivery set with first and second feeding tubes, an enteral feeding pump and a pinching mechanism for regulating the flow of nutrient formula or water out of the first and second feeding tubes), and a twin port adapter for use in the valve assembly. The twin port adapter includes a body configured to receive the first and second feeding tubes therein, and a feeding tube guide rotatably connected to the body and configured to secure the first and second feeding tubes within the body.

22 Claims, 18 Drawing Sheets

Related U.S. Application Data continuation-in-part of application No. 17/820,385, filed on Aug. 17, 2022, now Pat. No. 11,896,798.

(60) Provisional application No. 63/355,291, filed on Jun. 24, 2022, provisional application No. 63/280,405, filed on Nov. 17, 2021, provisional application No. 63/234,451, filed on Aug. 18, 2021.

(51) Int. Cl.
*A61M 39/22* (2006.01)
*A61M 39/10* (2006.01)
*A61M 39/24* (2006.01)

(52) U.S. Cl.
CPC ..... *A61M 39/28* (2013.01); *A61M 2039/1077* (2013.01); *A61M 39/223* (2013.01); *A61M 2039/248* (2013.01); *A61M 2039/2486* (2013.01)

(56) References Cited

U.S. PATENT DOCUMENTS

| | | | |
|---|---|---|---|
| 4,723,948 A | 2/1988 | Clark et al. | |
| 4,783,045 A | 11/1988 | Tartaglino | |
| 4,878,646 A | 11/1989 | Edelman et al. | |
| 5,007,803 A | 4/1991 | Divito et al. | |
| 5,026,020 A | 6/1991 | Betush | |
| D318,718 S | 7/1991 | Blatt | |
| 5,385,372 A * | 1/1995 | Utterberg | A61M 39/20 285/391 |
| 5,429,485 A | 7/1995 | Dodge | |
| 6,488,660 B1 | 12/2002 | Futterknecht | |
| 6,632,073 B2 | 10/2003 | Newcomer | |
| 6,749,090 B2 | 6/2004 | Bailey | |
| D523,553 S | 6/2006 | Beck et al. | |
| D578,209 S | 10/2008 | Schurg et al. | |
| 7,896,310 B2 | 3/2011 | Johansson et al. | |
| 8,152,780 B2 | 4/2012 | Evans et al. | |
| D672,455 S | 12/2012 | Beck | |
| 8,387,943 B1 | 3/2013 | Mattheis | |
| 8,425,470 B2 | 4/2013 | Beck et al. | |
| 8,807,517 B2 | 8/2014 | Townsend | |
| 8,876,787 B2 | 11/2014 | Beck et al. | |
| D745,963 S | 12/2015 | Mollstam et al. | |
| 9,707,068 B2 | 7/2017 | Drager et al. | |
| 9,976,545 B2 | 5/2018 | Glauber et al. | |
| 10,174,849 B2 | 1/2019 | Javaheri | |
| 10,376,447 B2 | 8/2019 | Besser et al. | |
| 11,213,460 B2 | 1/2022 | O'Keefe et al. | |
| 2003/0212381 A1 | 11/2003 | Whitehead, III | |
| 2004/0097903 A1 | 5/2004 | Raulerson | |
| 2005/0267418 A1 | 12/2005 | Fournie et al. | |
| 2006/0167415 A1 | 7/2006 | Nemoto | |
| 2009/0270842 A1 | 10/2009 | Blocher et al. | |
| 2010/0211022 A1 | 8/2010 | Harr et al. | |
| 2013/0277443 A1 * | 10/2013 | Croll | A61M 16/0463 239/589 |
| 2014/0249412 A1 | 9/2014 | Yamamoto | |
| 2017/0120039 A1 | 5/2017 | Childs et al. | |
| 2018/0216539 A1 | 8/2018 | Widener et al. | |
| 2018/0245699 A1 | 8/2018 | Lee | |
| 2018/0360695 A1 | 12/2018 | Jedwab et al. | |
| 2019/0388618 A1 | 12/2019 | Biermann et al. | |
| 2020/0000682 A1 * | 1/2020 | Hoffstetter | A61J 15/0076 |
| 2020/0085696 A1 | 3/2020 | Harr | |
| 2020/0096120 A1 | 3/2020 | Bargh | |
| 2020/0179671 A1 * | 6/2020 | Geppert | A61M 39/1011 |
| 2020/0393336 A1 | 12/2020 | Jones et al. | |
| 2021/0000694 A1 | 1/2021 | Bauer et al. | |
| 2021/0212903 A1 | 7/2021 | Okeefe et al. | |
| 2021/0298995 A1 | 9/2021 | Elia et al. | |
| 2023/0363981 A1 | 11/2023 | Sacchetti et al. | |

FOREIGN PATENT DOCUMENTS

| | | |
|---|---|---|
| EP | 1604699 B1 | 7/2014 |
| EP | 2108086 B1 | 8/2018 |
| JP | 2008208879 A | 9/2008 |
| WO | 2021055804 A1 | 3/2021 |

OTHER PUBLICATIONS

International Search Report and Written Opinion received for PCT Patent Application No. PCT/US2023/067642, mailed on Feb. 26, 2024, 12 pages.

EP23827945.9—Extended European Search Report Mailed on Apr. 8, 2026, 7 pages.

* cited by examiner

ENTERAL FEEDING PUMP SYSTEMS, VALVE ASSEMBLIES THEREFOR AND FLUID FLOW CONTROL METHODS FOR SAME

CROSS REFERENCE TO RELATED APPLICATIONS

This application is a continuation of application Ser. No. 18/325,985 filed May 30, 2023, Patented U.S. Pat. No. 11,992,464 which is a continuation-in-part of U.S. patent application Ser. No. 17/820,385, filed Aug. 17, 2022, and claims the benefit of priority to (1) U.S. Provisional Patent Application No. 63/234,451, filed Aug. 18, 2021, (2) U.S. Provisional Patent Application No. 63/280,405, filed Nov. 17, 2021, and (3) U.S. Provisional Patent Application No. 63/355,291, filed Jun. 24, 2022, the disclosures of all of which are incorporated by reference herein in their entireties.

FIELD OF THE INVENTION

Embodiments of the present invention relate to enteral feeding pump systems, and more particularly, to adapters for valve assemblies for use with enteral feeding pump systems.

BACKGROUND OF THE INVENTION

In general, enteral feeding pump systems are used to supply fluid nutrition to patients who are unable to eat. The pumping system typically includes a pump and disposable tubing sets (see, e.g., FIG. 1). An enteral feeding pump may be designed to pump only liquid nutrient formula or nutrient formula and water, separately.

In order to maintain cleanliness and prevent contamination of the liquids being pumped, any component directly in contact with liquid must be disposable.

BRIEF SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In an aspect of the invention, a flow selector valve assembly for an enteral feeding pump system is disclosed. The valve assembly includes a twin port adapter having first and second feeding tubes, the twin port adapter having a body, including first and second input ports each configured to receive a portion of the first and second feeding tubes therein, respectively; and an output port in communication with the first and second input ports; and a feeding tube guide rotatably connected to the body and configured to secure the first and second feeding tubes within the body. The twin port adapter is configured to position the first and second input ports in relation with a receiver, the receiver having a central shaft with an eccentric bearing such that at least a portion of the central shaft is received by and within the twin port adapter, the receiver configured to receive the twin port adapter with the central shaft positioned between the first and second input ports while the eccentric bearing is in a first position in which neither of the first and second input ports is compressed. The eccentric bearing is moveable between the first position, a second position rotated 90 degrees clockwise from the first position in which the eccentric bearing compresses the first input port therein to prevent flow therethrough, and a third position rotated 90 degrees counterclockwise from the first position in which the eccentric bearing compresses the second input port therein to prevent flow therethrough, and wherein the eccentric bearing is configured to be actuated by a digitally controlled motor within the enteral feeding pump system.

In another aspect of the invention, a twin port adapter for use in an enteral feeding pump system having first and second feeding tubes is disclosed. The twin port adapter comprises a body, including a U-shaped portion having a lower end with first and second sides and an upper end with first and second sides, first and second input ports formed in the lower end and each configured to receive a portion of the first and second feeding tubes therein, respectively, and an output port in communication with the first and second input ports. The twin port adapter further comprises a feeding tube guide rotatably connected to the first side of the upper end and configured to secure the first and second feeding tubes within the body.

In yet another aspect of the invention, a twin port adapter for use in an enteral feeding pump system having first and second feeding tubes is disclosed. The twin port adapter comprises a body, including a U-shaped portion having a lower end with first and second sides and an upper end with first and second sides, first and second input ports formed in the lower end and each configured to receive a portion of the first and second feeding tubes therein, respectively, and an output port in communication with the first and second input ports. The twin port adapter further comprises a feeding tube guide rotatably connected to the first side of the upper end, and configured to secure the first and second feeding tubes within the body, the feeding tube guide including first and second ends, and first and second C-shaped tube-receiving members positioned between the first and second ends and configured to receive and secure the first and second feeding tubes therein, respectively. The first C-shaped tube-receiving member includes a first protrusion configured to engage the first feeding tube, and the second C-shaped tube-receiving member includes a second protrusion configured to engage the second feeding tube. The central wall includes a third protrusion opposite the first protrusion and configured to engage the first feeding tube, and a fourth protrusion opposite the second protrusion and configured to engage the second feeding tube.

These and other features and advantages will be apparent from a reading of the following detailed description and a review of the associated drawings. It is also to be understood that both the foregoing general description and the following detailed description are explanatory only and not restrictive of aspects as claimed.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings.

DETAILED DESCRIPTION OF THE INVENTION

It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

Enteral Feeding Pump Pinch Valves

Disclosed herein are pinch valves for with an enteral feeing pump systems. Such a system is shown in FIG. 1.

Figure 1:
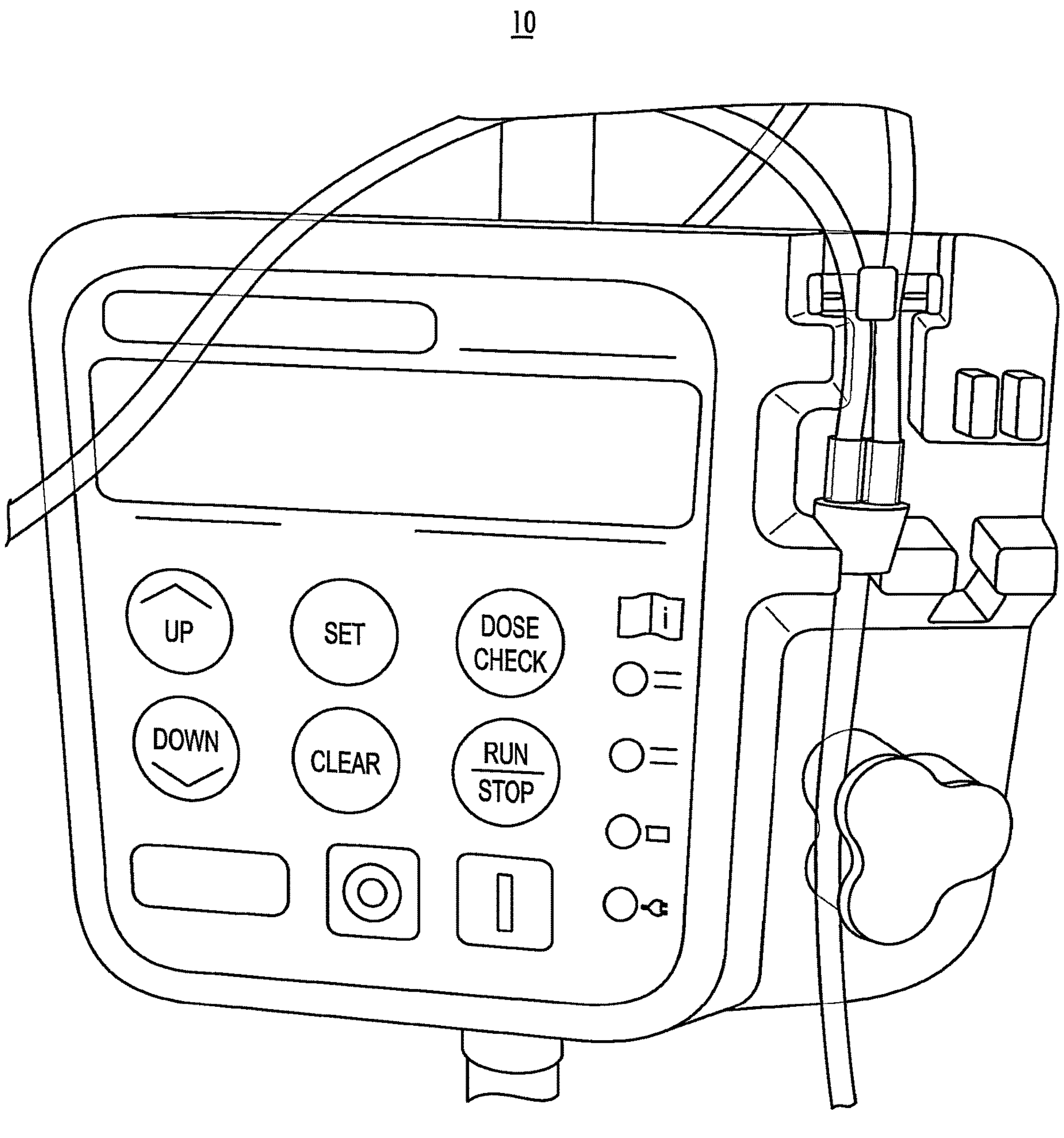
FIG. 1 is a front view of an exemplary motor of an exemplary enteral feeding pump system.

As shown in FIG. 1, an exemplary motor 10 that is part of an exemplary enteral feeding pump system is illustrated and includes a disposable fluid delivery set with two separate source containers connected by tubing to a tubing adapter that combines flow from the two separate tubes into a single fluid stream, an integral peristaltic tube section, and an enteral feeding pump. The enteral feeding pump motor 10 includes a rotor that engages the peristaltic tube section and, when rotated, causes liquid to flow in a direction of rotation, wherein the tubing from the two fluid source containers passes through a pinching mechanism for selectively closing or opening a flow of fluid from either container into a patient. In various embodiments, the pinching mechanism is actuated by an inflatable bladder linked to a micro air pump, or an inflatable bellows linked to a micro air pump. In a preferred embodiment, the inflatable bellows operates in the pressure range of 0.1 to 1 bar.

Figure 2:
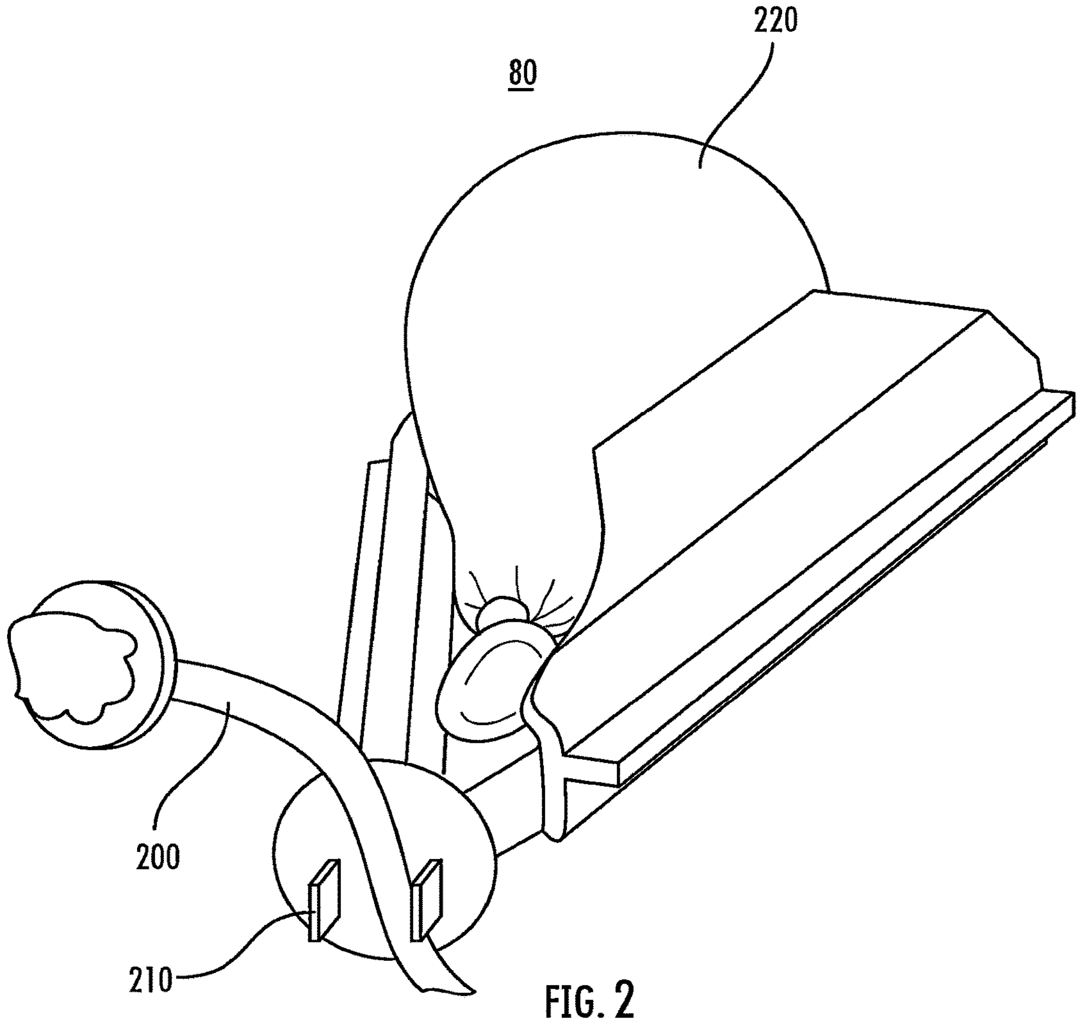
FIG. 2 illustrates a first embodiment of an exemplary pinching mechanism.

As shown in FIG. 2, a first embodiment of an exemplary pinching mechanism 80 includes tubing 200 residing within a single pincher 210. A tightening and loosening of the single pincher 210 about the tubing 200 is controlled with an inflatable bladder 220, shown here in an inflated condition. The inflatable bladder 200 is connected to a micro air pump (not shown). In operation, the micro air pump inflates the inflatable bladder 200, causing the single pincher 210 to constrict around the tubing 200. When the tubing 200 is constricted, no fluid flows within the tubing 200. When the micro air pump deflates the inflatable bladder 200, the single pincher 210 releases its grip on the tubing 200 and fluid flow within the tubing 200 is enabled.

In another embodiment, the pinching mechanism is controlled via an inflatable bellows linked to the micro air pump. In a preferred embodiment, the inflatable bellows operates in the pressure range of 0.1 to 1 bar.

Figure 3:
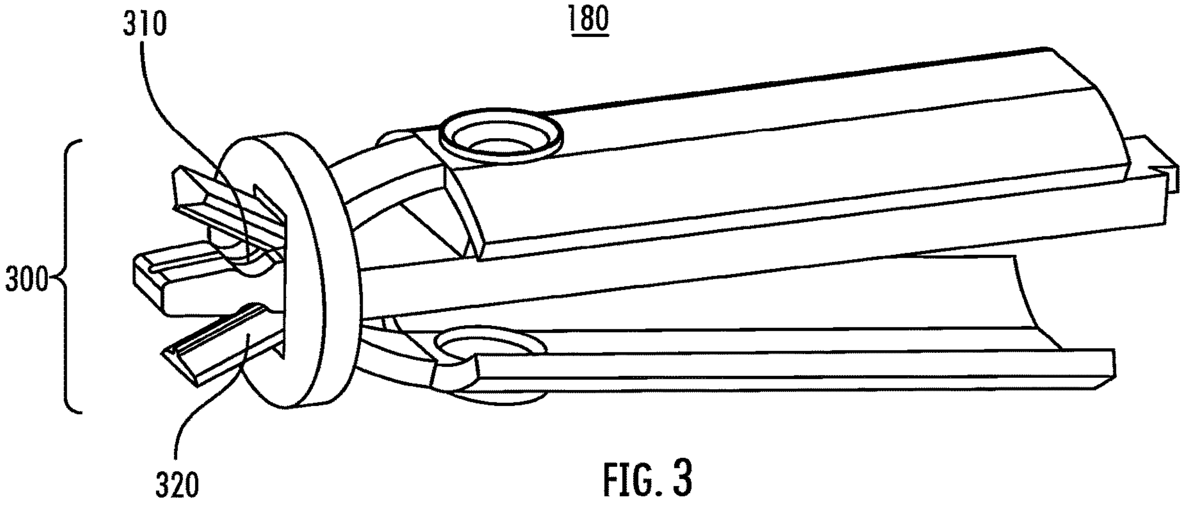
FIG. 3 illustrates a second embodiment of an exemplary pinching mechanism.

As shown in FIG. 3, a second embodiment of an exemplary pinching mechanism 180 includes pincher 300 having a first channel 310 and a second channel 320, The dual pincher channels 310, 320 enable placement on tubing (not shown) in both. A tightening and loosening of the pincher 300 about tubing in the channels 310, 320 is controlled with an inflatable bladder (not shown) connected to a micro air pump (not shown). When the micro air pump inflates the inflatable bladder, the first channel 310 and a second channel 320 clap down over the tubing, preventing fluid flow within the tubing. When the micro air pump deflates the inflatable bladder, the pincher 300 releases its grip on the tubing 200 and fluid flow within the tubing in the channels 310, 320 is enabled.

In another embodiment, the inflatable bladder is replaced by an inflatable bellows linked to the micro air pump. In a preferred embodiment, the inflatable bellows operates in the pressure range of 0.1 to 1 bar.

Figure 4:
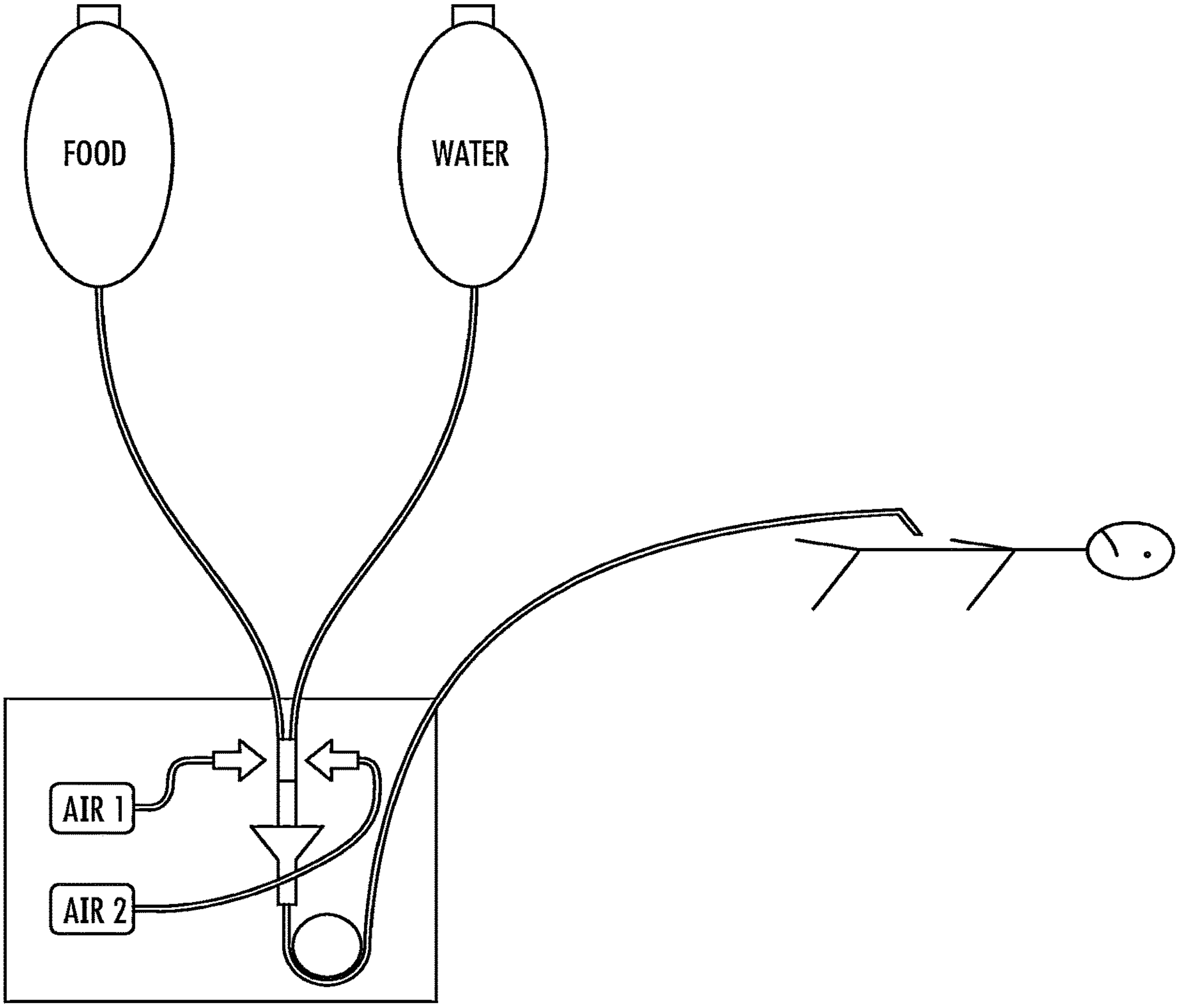
FIG. 4 is a schematic illustration of an exemplary double pinch system.

FIG. 4 is a schematic illustration of an exemplary double pinch system.

Figure 5:
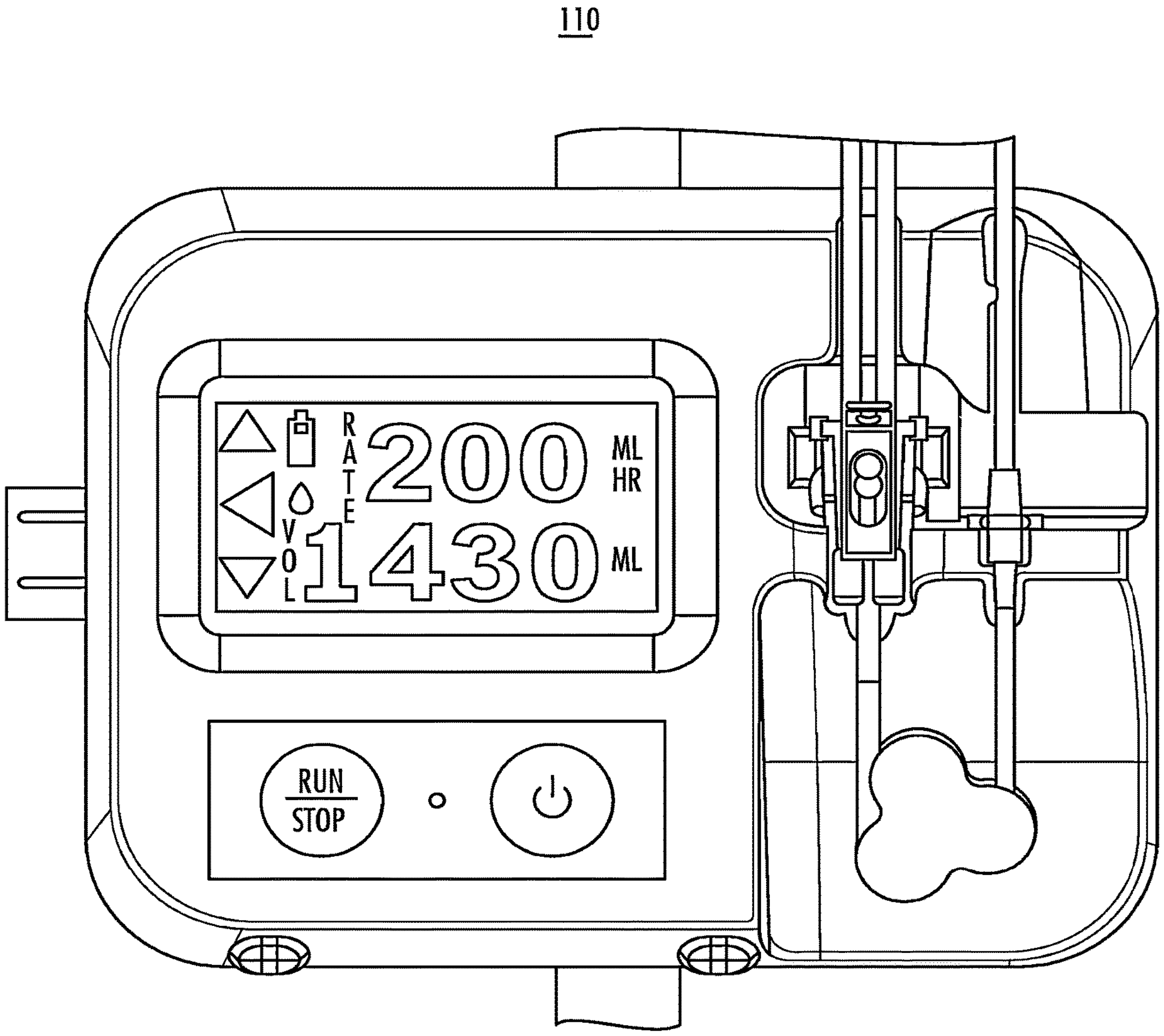
FIG. 5 is a front view of another exemplary enteral feeding pump system.

As shown in FIG. 5, an exemplary enteral feeding pump system 110 is illustrated and includes a disposable fluid delivery set with two separate source containers connected by tubing to a tubing adapter that combines flow from the two separate tubes into a single fluid stream, an integral peristaltic tube section, and an enteral feeding pump. The enteral feeding pump includes a rotor that engages the peristaltic tube section and, when rotated, causes liquid to flow in a direction of rotation, wherein the tubing from the two fluid source containers passes through an eccentric pinching mechanism for selectively closing or opening a flow of fluid from either container into a patient, the eccentric pinching mechanism actuated by one quadrant clockwise or one quadrant counterclockwise motor rotation.

Figure 6:
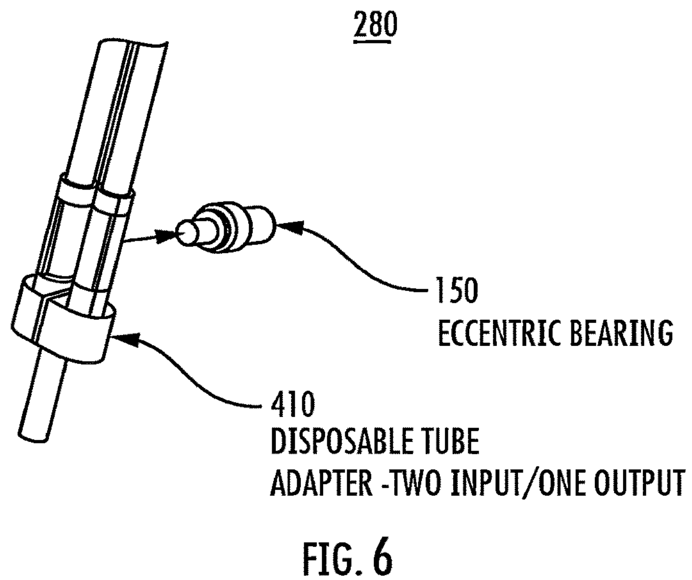
FIG. 6 illustrates an embodiment of exemplary pinching mechanism components.

As shown in FIG. 6, a first embodiment of an exemplary pinching mechanism 280 includes two flexible tubes (typically PVC or other flexible material), residing within the flow selector adapter 410. When the adapter is installed onto the eccentric bearing 150, it forms the pinch valve system.

Figure 7:
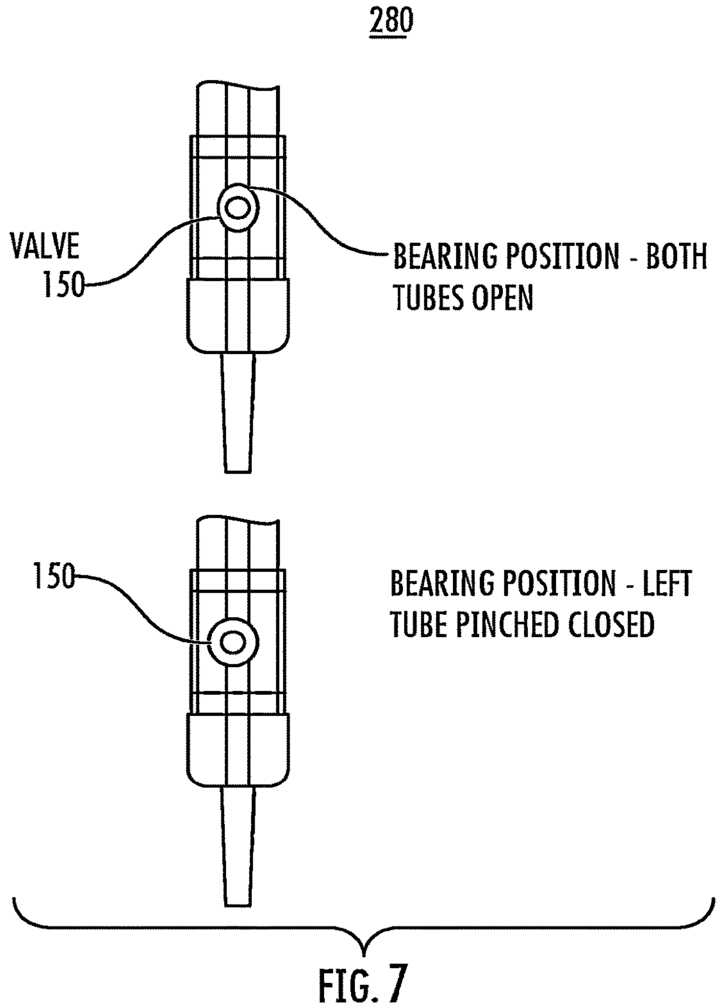
FIG. 7 illustrates a third embodiment of an operating exemplary pinching mechanism.

As shown in FIG. 7, two views of the exemplary pinching mechanism 280 include firstly, the eccentric bearing 150 oriented in the central (neutral) position to accommodate adapter installation and, second, the eccentric bearing 150 rotated 90 degrees with sufficient force to pinch and stop fluid flow through either intervening tube. Reversing the rotation allows flow to resume through the tube. With rotation continuing 180 degrees (90 degrees beyond center position), the second intervening tubing section is pinched and fluid flow is stopped.

Figure 8:
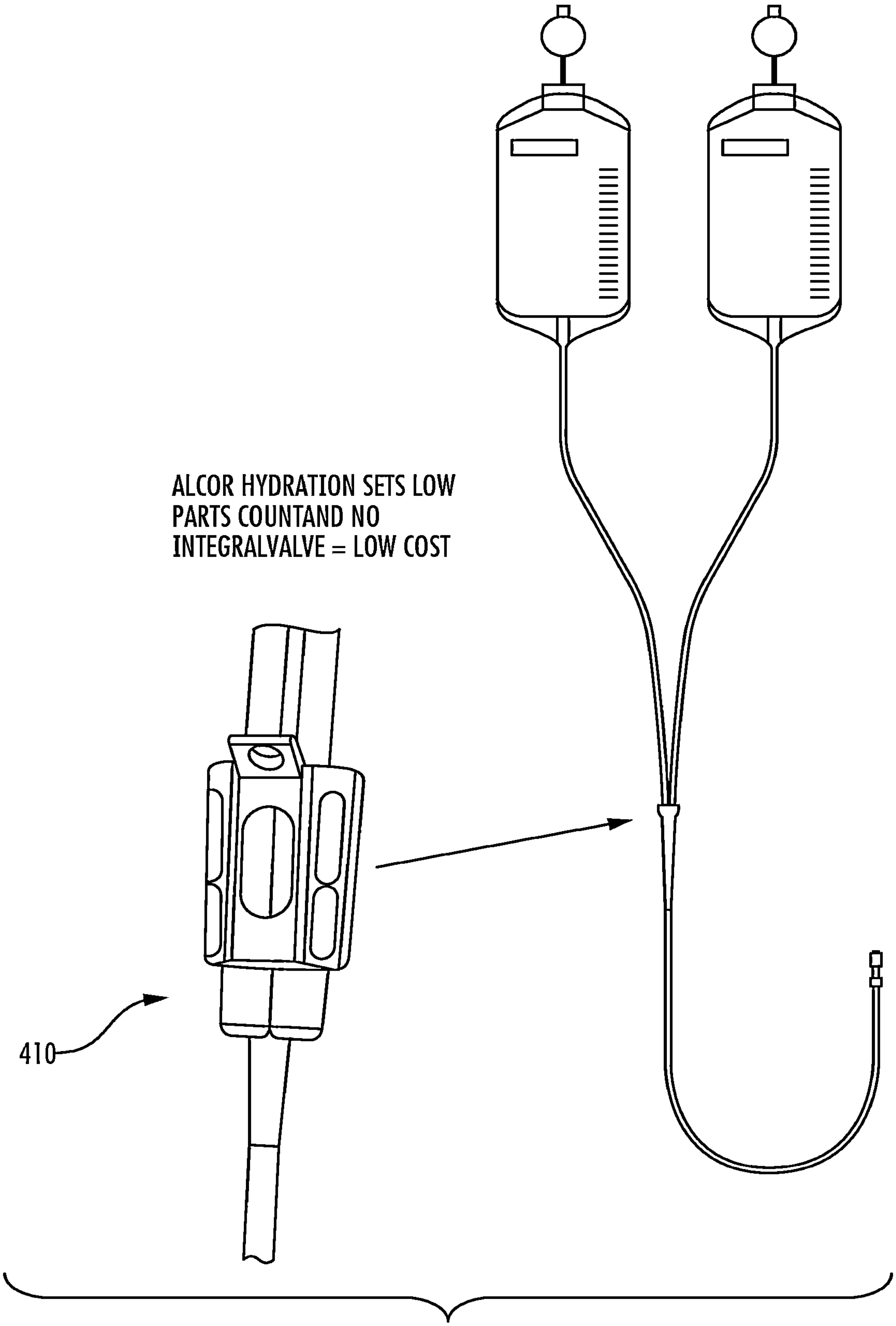
FIG. 8 illustrates an exemplary disposable tubing set with an adapter that enables selective pinching of formula or water tubes.
Figure 9:
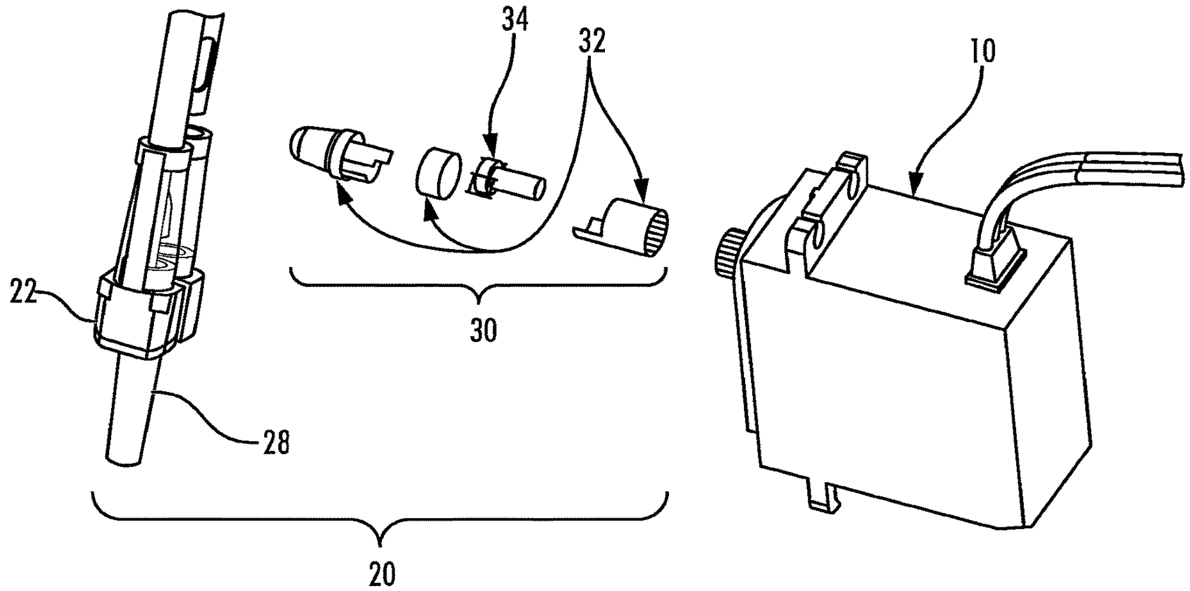
FIG. 9 is an exploded view of a flow selector valve system according to the present invention.

FIG. 8 illustrates an exemplary disposable tubing set with adapter 410 that enables fluid flow from either selected source.

Flow Selector Valve Assemblies and Operation of Same

Also disclosed herein are flow selector valve assemblies for use with an enteral feeing pump.

Referring again to FIG. 1, an exemplary motor 10 of an exemplary enteral feeding pump constitutes a durable actuator and is illustrated and is used with a disposable fluid delivery set with two separate source containers connected by tubing to a tubing adapter that combines flow from the two separate tubes into a single fluid stream, and an integral peristaltic tube section (see FIGS. 9 and 10A-10C). The enteral feeding pump motor 10 includes a motor that engages a disposable tube adapter and, when rotated, controls the fluid flow through one of two tubes, as described below.

FIGS. 9, 10A-C and 11A-11D illustrate an exemplary flow selector valve assembly 20 of the present invention that is used with the enteral feeding pump motor 10 of FIG. 1. The flow selector valve assembly 20 is operatively connected to the enteral feeding pump motor 10, as further described below.

As shown in FIGS. 9, 10A-C and 11A-11D, the enteral feeding pump motor 10 engages the flow selector valve assembly 20 according to an embodiment of the present invention. The flow selector valve assembly 20 includes a disposable tube adapter 22 (i.e., a disposable set section) having two input flexible tubing channels 24, 26 and one output tubing channel 28. The two input tubing channels 24, 26 are configured to receive two respective tubes 24*a*, 24*b* connected to two fluid sources (not shown). The output tubing channel 28 is configured to receive a feeding tube (i.e., an integral peristaltic tube section) that is inserted into a patient to provide the fluids/nutrients (not shown).

The disposable tube adapter 22 (i.e., set section) is easily installed (as part of the flow selector valve assembly 20) on the enteral feeding pump motor 10 (i.e., durable actuator).

Figure 11A:
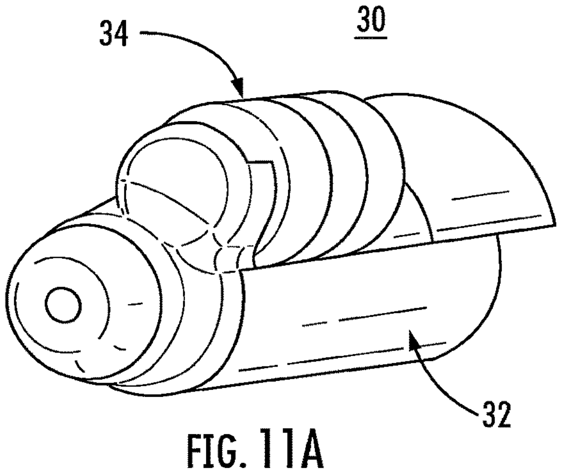
FIG. 11A is a detailed top perspective view of an eccentric bearing of the system of FIGS. 9-10C.

The flow selector valve assembly 20 is configured to select either one of two fluid sources, or both simultaneously. The two input flexible tubing channels 24, 26 are separate from the mechanism that closes the fluid flow through either of them (i.e., their respective tubes 24*a*, 24*b*). The tube adapter 22 positions the flexible tubing channels 24, 26 in relation with a receiver 30. As illustrated in FIG. 11A, the receiver 30 has a central shaft 32 and an eccentric bearing 34 extending from a digitally controlled motor (e.g., in the feeding pump system 10).

Figure 10A:
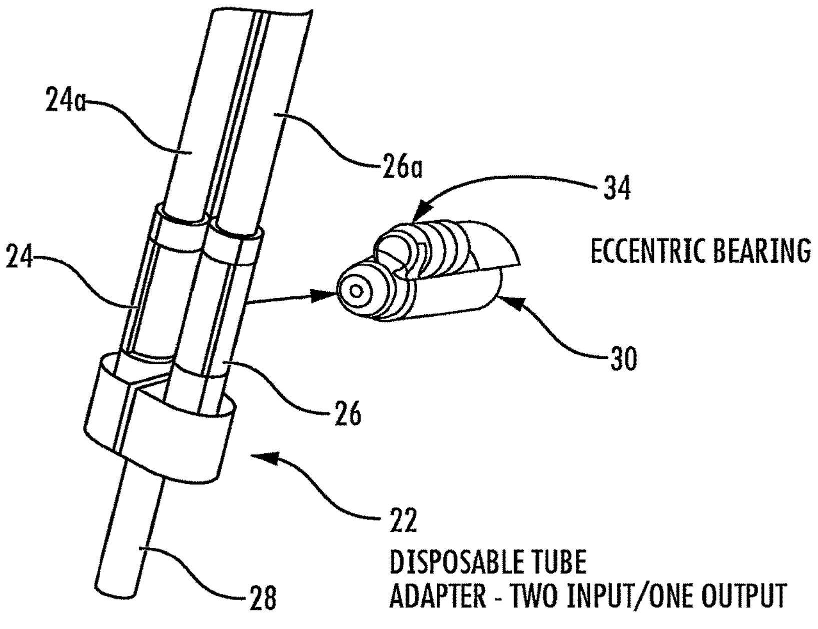
FIG. 10A is a top perspective, partially-exploded view of the system of FIG. 9.
Figure 10B:
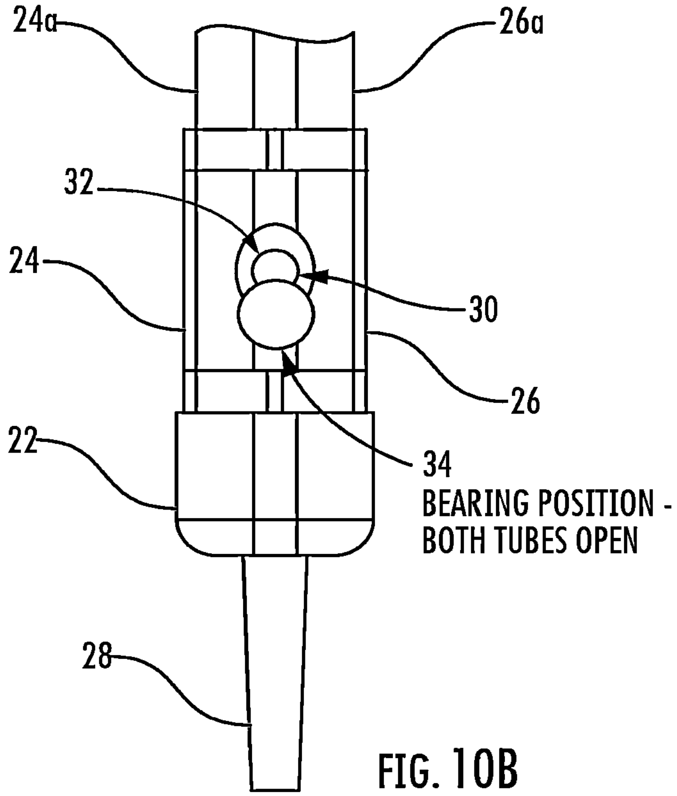
FIG. 10B is a plan view of the system of FIG. 9 in which both input flexible tubing channels/tubes of the system are open.
Figure 11B:
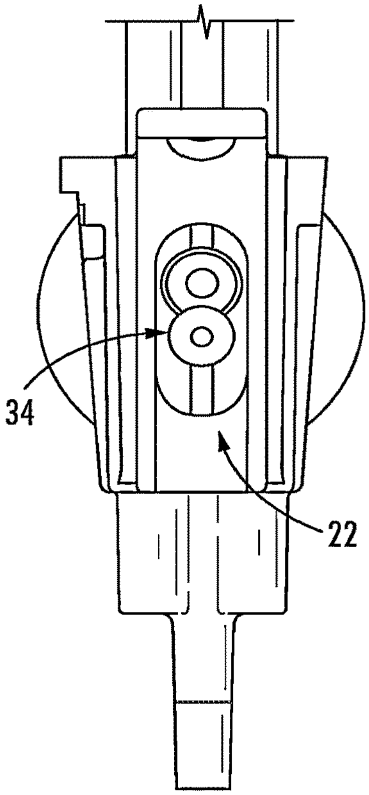
FIG. 11B is a plan view of the system of FIGS. 9-10C in a first position in which both input flexible tubing channels/tubes of the system are open.

As shown in FIGS. 10B and 11B, in operation, the bearing 34 is positioned at a 12 o'clock orientation, wherein neither of the input flexible tubing channels 24, 26 nor the respective tubes 24*a*, 26*a* therein is compressed. This position facilitates loading and unloading of the adapter 22/tubing assembly 20.

Figure 10C:
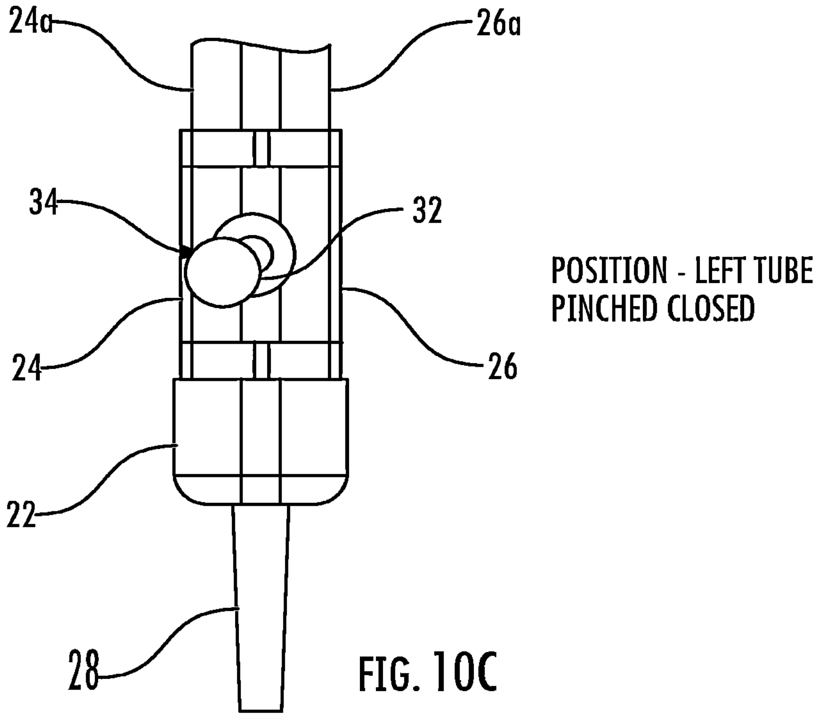
FIG. 10C is a plan view of the system of FIG. 9 in which one of the input flexible tubing channels/tubes of the system is pinched closed by the eccentric bearing.
Figure 11C:
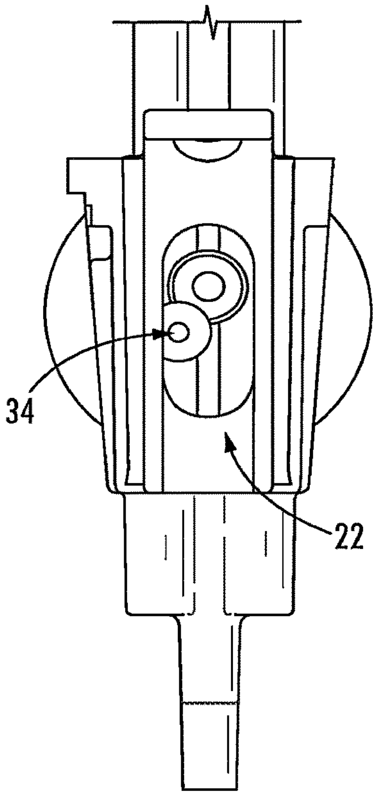
FIG. 11C is a plan view of the system of FIGS. 9-10C in a second position in which a first input flexible tubing channel/tube of the system is pinched closed by the eccentric bearing.
Figure 11D:
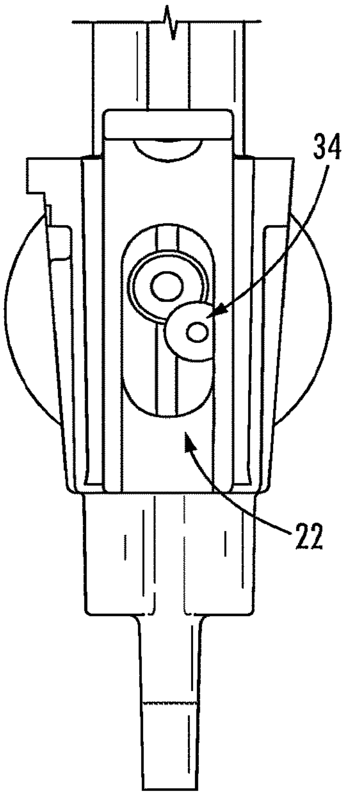
FIG. 11D is a plan view of the system of FIGS. 9-10C in a third position in which a second input flexible tubing channel/tube of the system is pinched closed by the eccentric bearing.

As shown in FIGS. 10C and 11C, when the bearing 34 is moved to the 9 o'clock position (e.g., by counterclockwise rotation of the motor of the feeding pump 10), the bearing 34 compresses the input flexible tubing channel 24, pinching the tube 24*a* therein closed and preventing flow therethrough. Similarly, when the bearing 34 is moved to the 3 o'clock position (e.g., by clockwise rotation of the motor of the feeding pump 10) as shown in FIG. 11D, the bearing 34 compresses the input flexible tubing channel 26, pinching the tube 26*a* therein closed and preventing flow therethrough.

The flow selector valve assembly 20 therefore operates in coordination with the enteral feeding pump motor 10 to selectively close one of the input flexible tubing channels 24, 26 and the respective tubes 24*a*, 26*a* therein.

One advantage of the invention disclosed herein is the ease of installation of the disposable tube adapter 22 (i.e., set section) on the enteral feeding pump motor 10 (i.e., durable actuator).

Twin Port Adapter and Operation of Same

Reference is now made to FIGS. 12-20, which illustrate an embodiment of a twin port adapter (TPA) 500 for use with a flow selector valve assembly (including a pinch valve thereof) and feeding pump system according to the present invention. As shown in FIGS. 12-15, the TPA 500 includes a body having a U-shaped portion 502 having first (i.e., lower) and second (i.e., upper) ends 504, 506. The lower end 504 includes first and second (e.g., left and right) sides 504*a*, 504*b*, and the upper end 506 includes first and second (e.g., left and right) sides 506*a*, 506*b*. The TPA body further includes input ports (i.e., input tubing channels) 508*a*, 508*b* formed in the lower end 504 of the U-shaped portion 502 (i.e., between the left and rights sides 504*a*, 504*b* thereof) and extending downward therefrom, an output port (i.e., output tubing channel) 510 in communication with the input ports 504*a*, 504*b*, and a thumb handle 512 extending from the upper end 506 of the U-shaped portion 502 (i.e., between the left and rights sides 506*a*, 506*b* thereof) for mounting the TPA 500 in the feeding pump system and otherwise handling and manipulating the TPA 500.

With continued reference to FIGS. 12-16 and 19, the TPA 500 further includes a movable feeding tube guide 514. The feeding tube guide 514 includes a first end 516, a second end 518 opposite the first end 516. The second end 518 is configured to securely engage the second side 506*b* of the upper end 506 of the U-shaped portion 502 (e.g., via a latch mechanism). The feeding tube guide 514 further includes adjoining first and second C-shaped tube-receiving members 520, 522 positioned between the first and second ends 516, 518 and configured to receive and secure flexible first and second feeding tubes 524, 526 of the feeding pump system therein (i.e., within the apertures formed thereby), respectively (see FIG. 16). The tube-receiving members 520, 522 each include first and second retainer bumps, or protrusions 521, 523, respectively, that are configured to engage the first and second feeding tubes 524, 526, respectively. The feeding tube guide 514 further includes a central Y-shaped wall 528 common to the first and second tube-receiving members 520, 522 that separates the respective apertures formed thereby. In the illustrated embodiment, the wall 528 is Y-shaped, and includes a third retainer bump, or protrusion, 530 extending into the aperture formed by the first tube-receiving member 520 (i.e., across from/opposite to the first protrusion 521), and a fourth retainer bump, or protrusion, 532 extending into the aperture formed by the second tube-receiving member 522 (i.e., across from/opposite to the second protrusion 523). The third and fourth protrusions 530, 532 are configured to engage the first and second feeding tubes 524, 526, respectively. Other configurations of the wall 528 are possible in alternate embodiments of the invention (e.g., not having a Y-shape).

Figure 12:
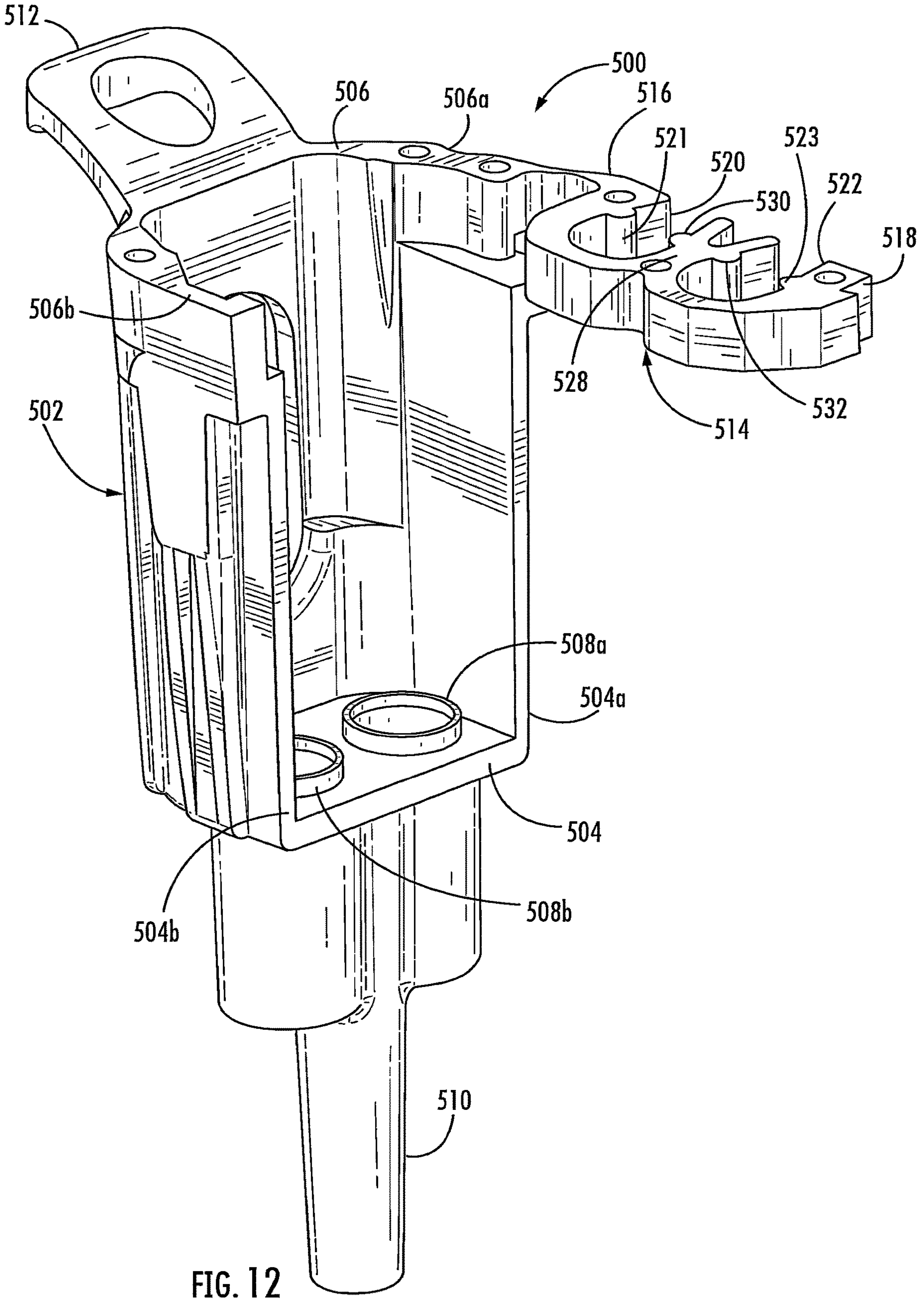
FIG. 12 is a right top perspective view of a twin port adapter according to the present invention, with a feeding tube guide in an opened position.
Figure 13:
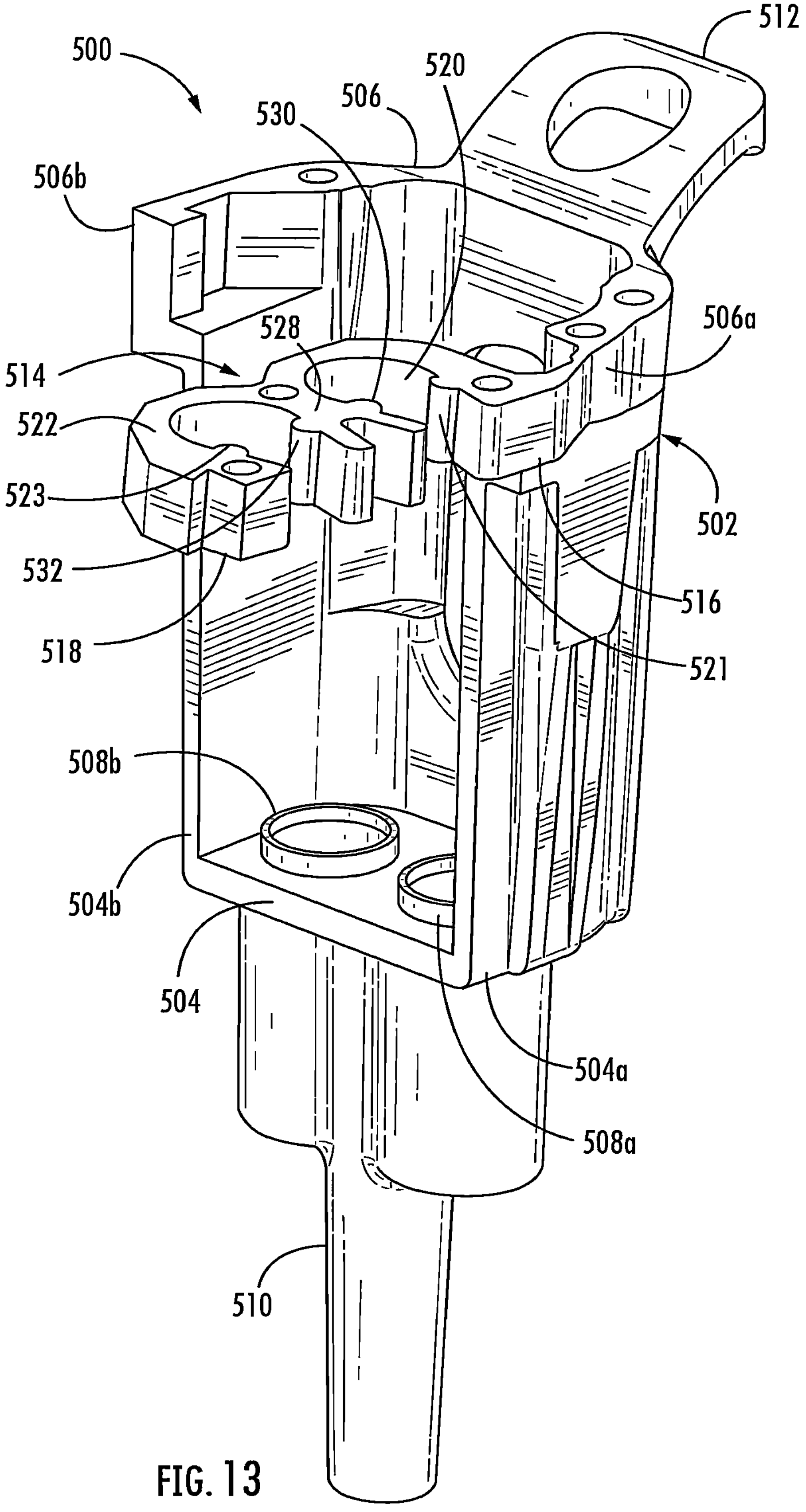
FIG. 13 is a left top perspective view of the twin port adapter of FIG. 12.
Figure 14:
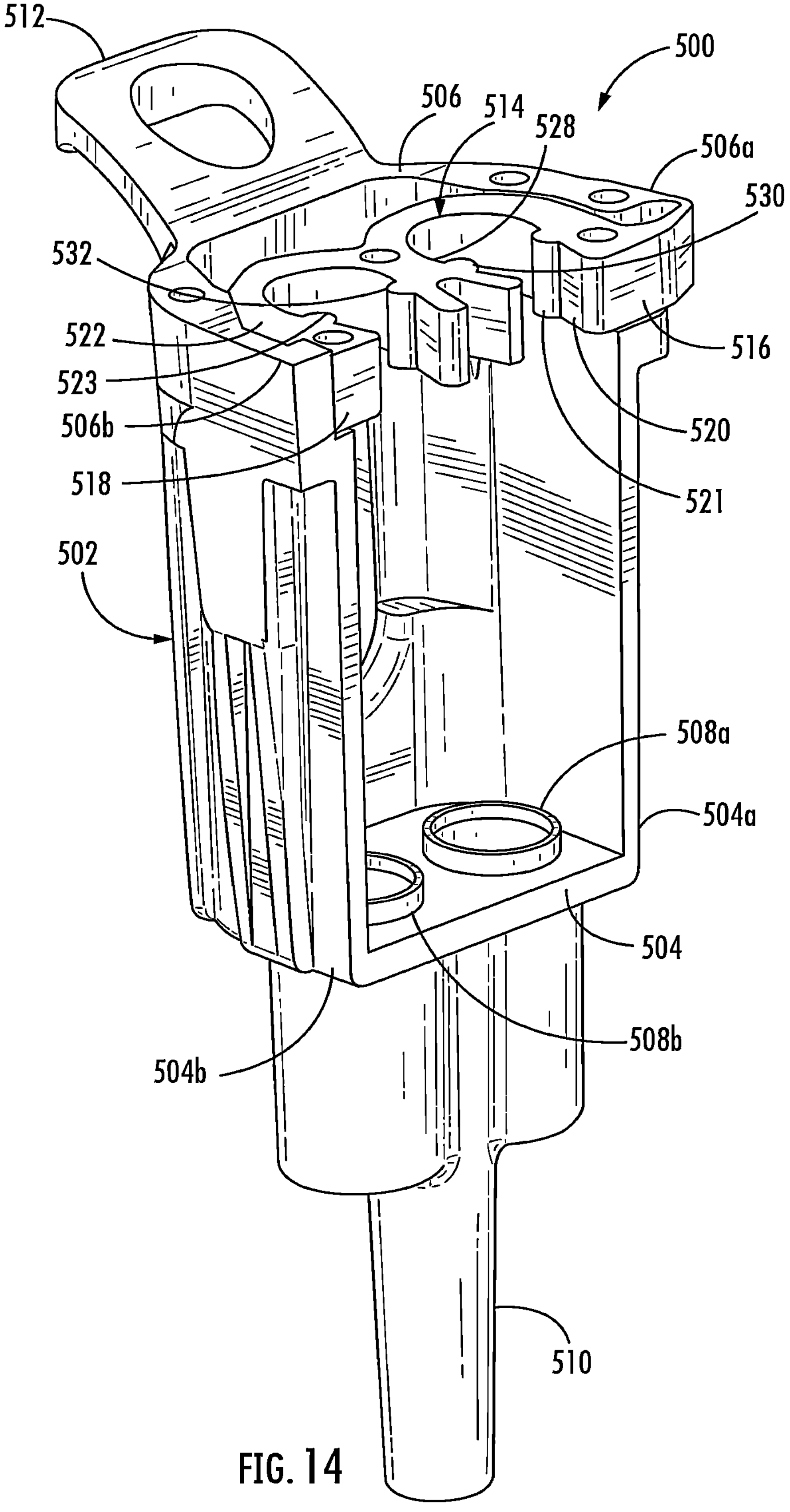
FIG. 14 is a right top perspective view of the twin port adapter according of FIG. 12, with the feeding tube guide in a closed position.
Figure 15:
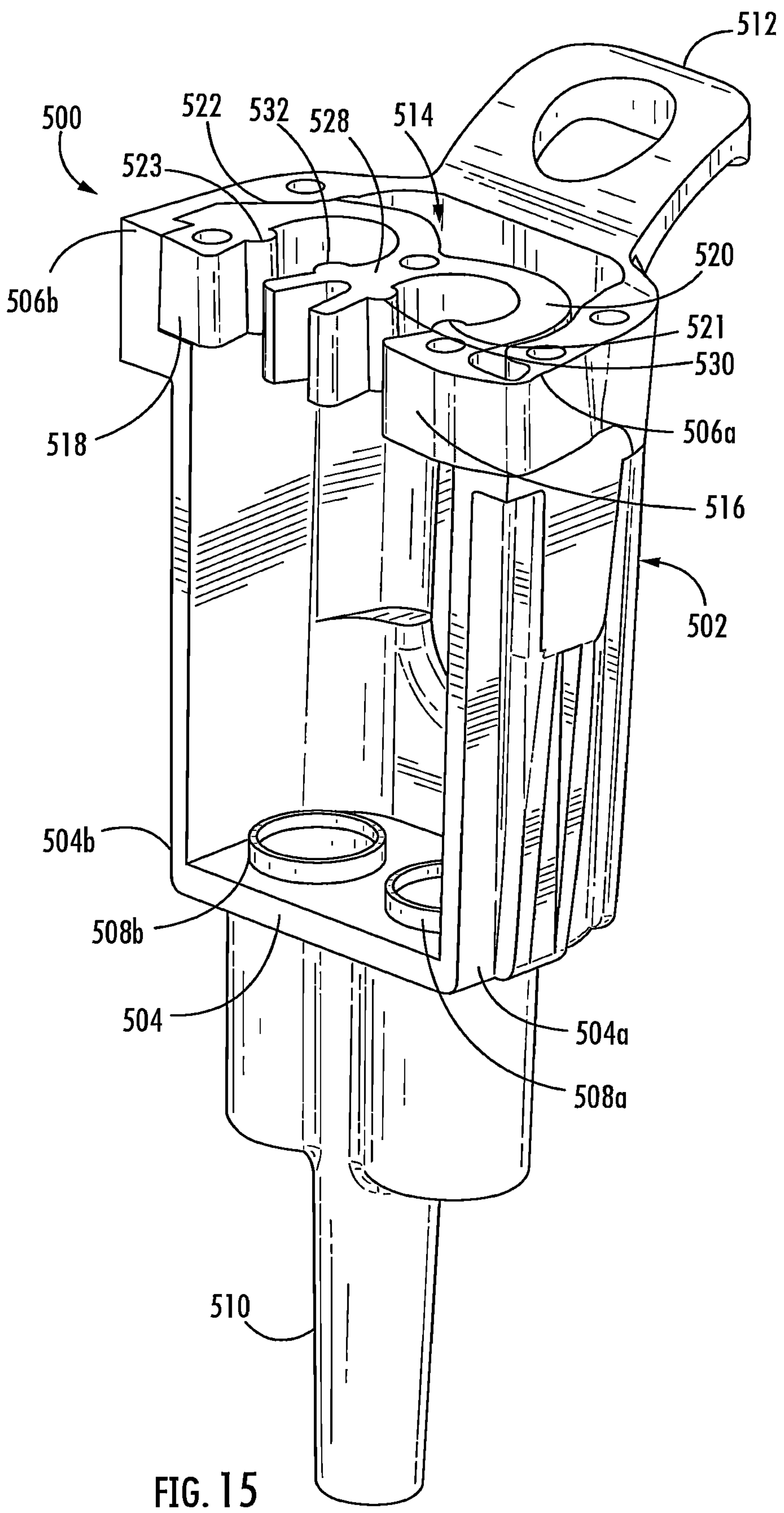
FIG. 15 is a left top perspective view of the twin port adapter of FIGS. 12 and 14, with the feeding tube guide in the closed position.
Figure 16:
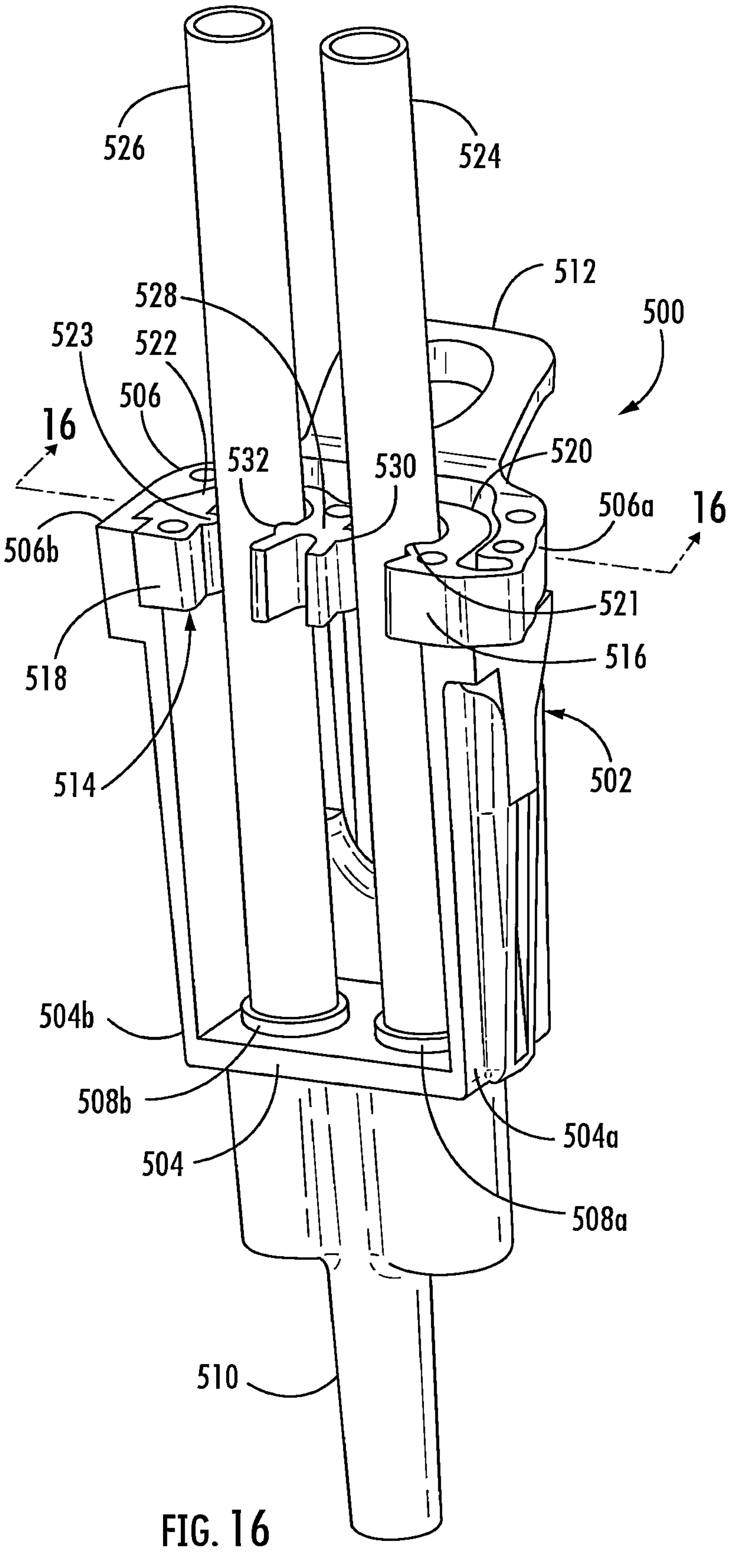
FIG. 16 is a top perspective view of the twin port adapter of FIGS. 12 and 14, in use with flexible feeding tubes.

The first end 516 of the feeding tube guide 514 is rotatably attached to the first side 506*a* of the upper end 506 of the U-shaped portion 502. In various embodiments, the first end 516 is attached to the first side 506*a* as a living hinge that is molded as a single-action tool, which enables the feeding tube guide 514 to swing out to the left or right. The feeding tube guide 514 is thereby moveable from an opened position, as shown in FIGS. 12 and 13, to a closed, or locked, position, as shown in FIGS. 14-17. In various embodiments, the feeding tube guide 514 serves to allow a simple straight pull injection mold in its open position/configuration. In various embodiments, the feeding tube guide 514 guide (once molded) is moved (i.e., folded) only once to its permanently closed/locked position.

Figure 20:
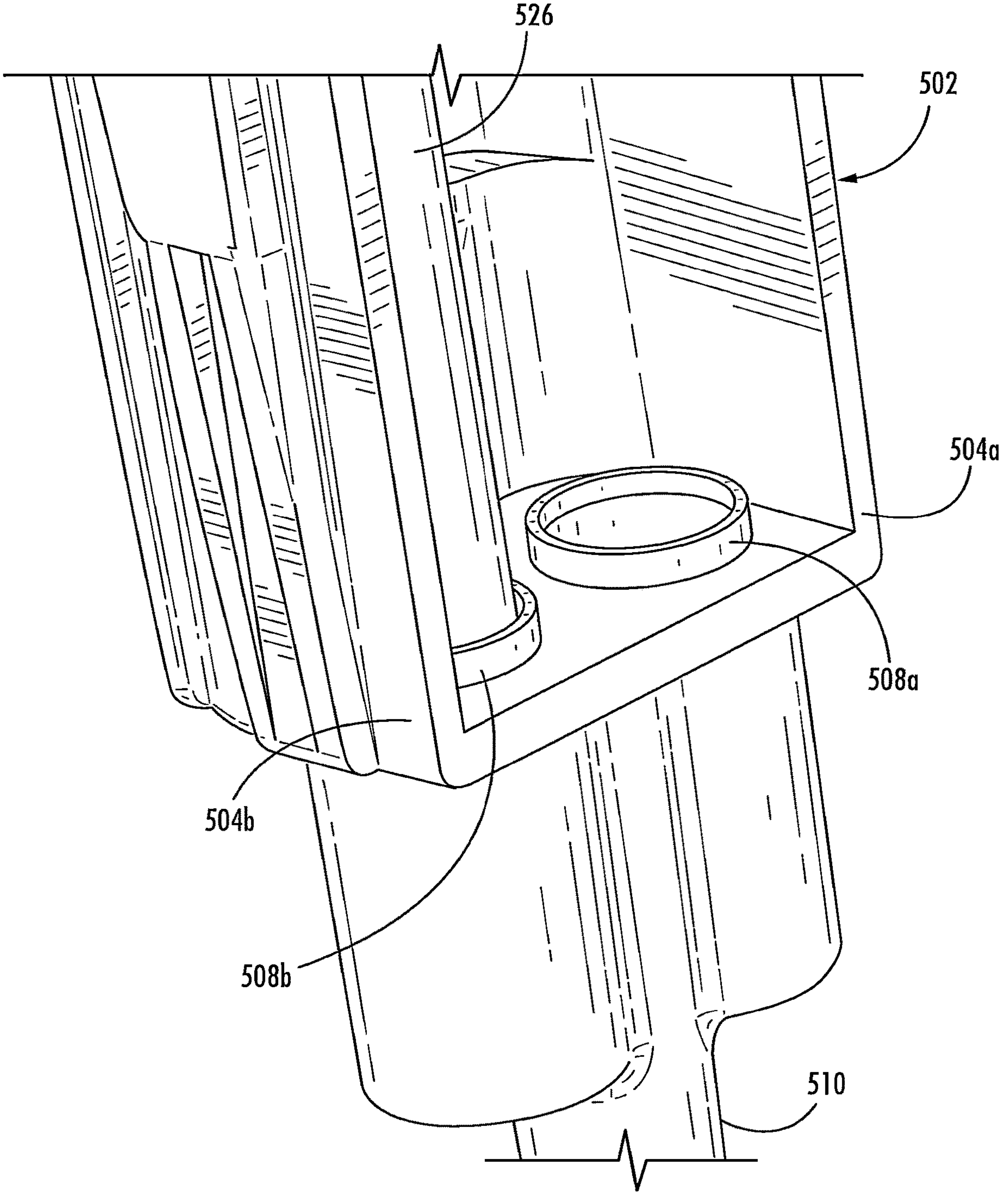
FIG. 20 is a detailed perspective top perspective view of the twin port adapter of FIG. 12.

With further reference to FIGS. 16, 17, 19 and 20, the first and second feeding tubes 524, 526 are shown secured to the TPA 500 within the respective apertures of the first and second C-shaped tube-receiving members 520, 522 of the feeding tube guide 514, and secured by the respective first and second protrusions 521, 523 and the third and fourth protrusions 530, 532 of the wall 528. The first and second feeding tubes 524, 526 are further secured to the TPA 500 by bonding the feeding tubes 524, 526 to the respective input ports 508*a*, 508*b* with an adhesive. This is illustrated in FIG. 20, wherein the feeding tube 526 is shown bonded to the inlet port 508*b*. The feeding tube 524 is similarly bonded to the inlet port 508*a* (not shown). In various embodiments, the feeding tubes 524, 526 are bonded to the respective input ports 508*a*, 508*b* by a UV-cured adhesive, a non-limiting example of which is Dymax 1405-M. The adhesive is applied to the portion of the feeding tubes 524, 526 to be bonded to the respective input ports 508*a*, 508*b* (i.e., the lower ends of each feeding tube), and the feeding tubes 524, 526 are inserted into the respective input ports 508*a*, 508*b*. The tubes 524, 526 and respective input ports 508*a*, 508*b* are then subjected to UV illumination with intensity and wavelength required to cure the applied adhesive, which cures (i.e., solidifies) the adhesive, thereby securing the lower ends of the feeding tubes 524, 526 to and within the respective input ports 508*a*, 508*b*. In various embodiments, the UV intensity ranges from 13 to 30 $W/cm^2$. In various embodiments, the UV wavelength ranges from 300 nm to 500 nm. As shown in FIG. 20, the first and second protrusions 521, 523 and the third and fourth protrusions 530, 532 of the wall 528 temporarily retain the feeding tubes 524, 526 while the adhesive is applied and cured. Once the adhesive is cured, the feeding tubes 524, 526 are pushed fully into the first and second C-shaped tube-receiving members 520, 522, respectively, of the feeding tube guide 514. The upper ends of the feeding tubes 524, 526 are not bonded in place, and are thereby repositionable to allow their movement in use.

In various embodiments, the TPA 500 is formed by injection molding.

In various embodiments, the TPA 500 is formed from rigid PVC or ABS. The TPA 500 may also be formed from other suitable polymers and materials.

Figure 17:
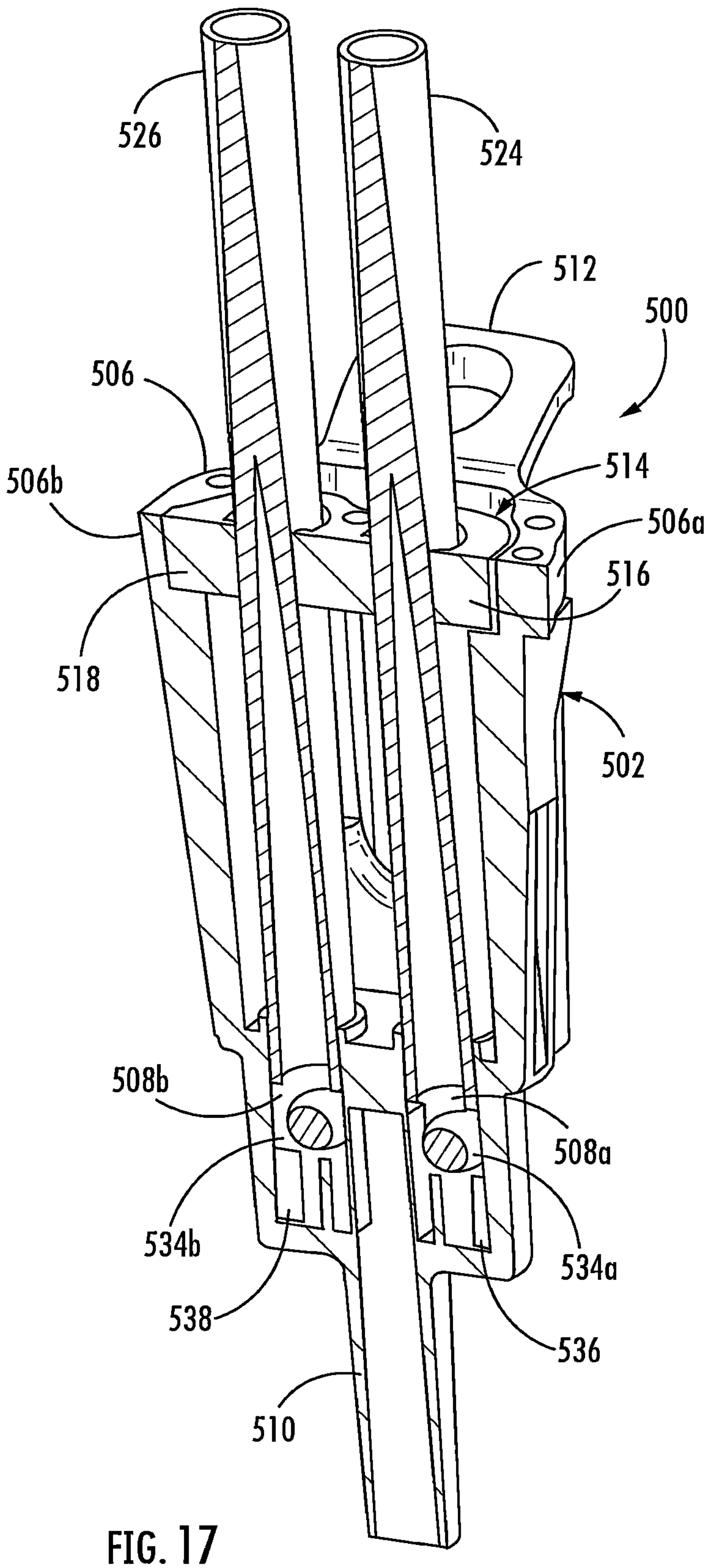
FIG. 17 is a top perspective cross-sectional view of the twin port adapter of FIGS. 12, 14 and 16, taken along lines 16-16 of FIG. 16.
Figure 18:
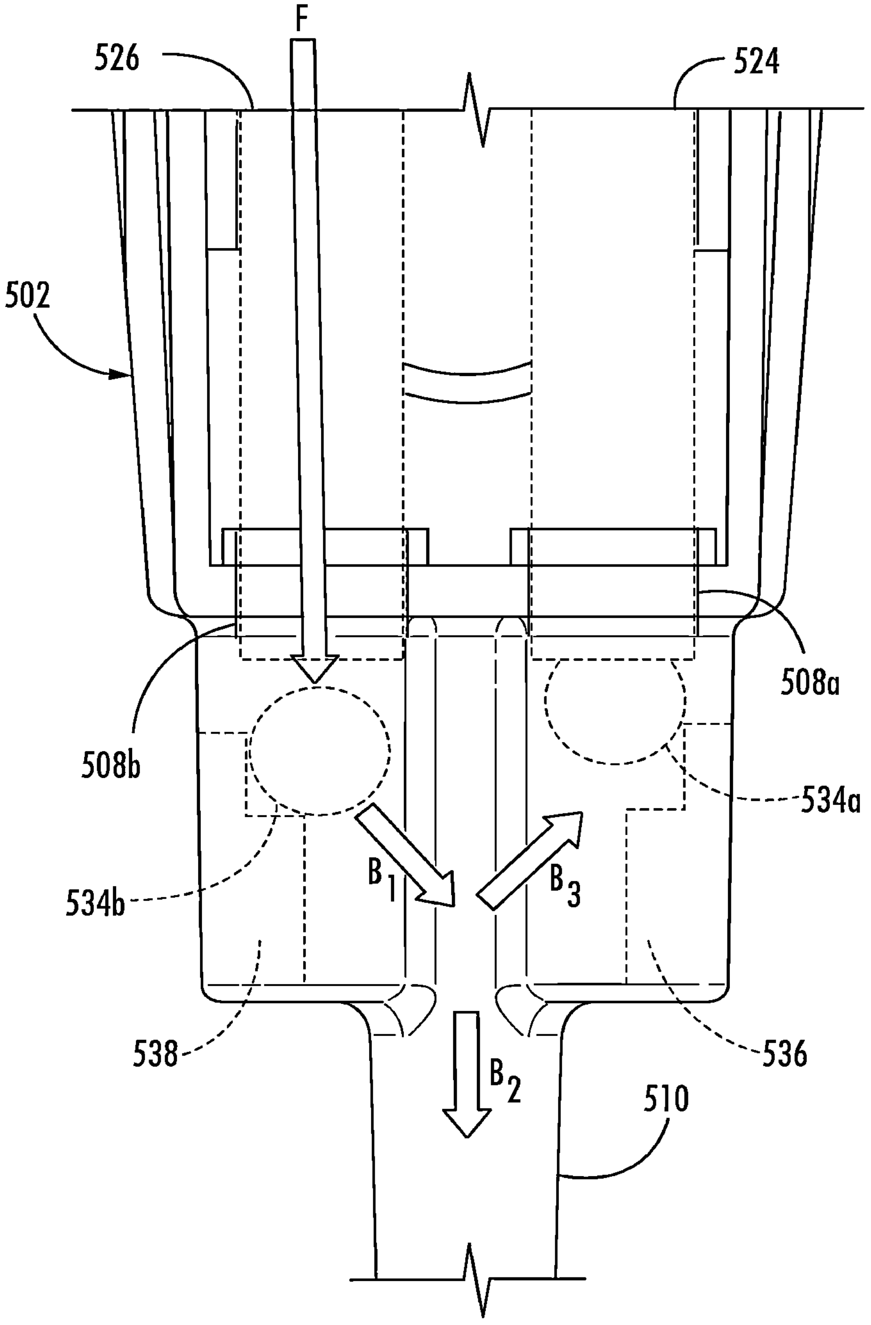
FIG. 18 is a detailed view of the twin port adapter of FIGS. 12, 14, 16 and 17.
Figure 19:
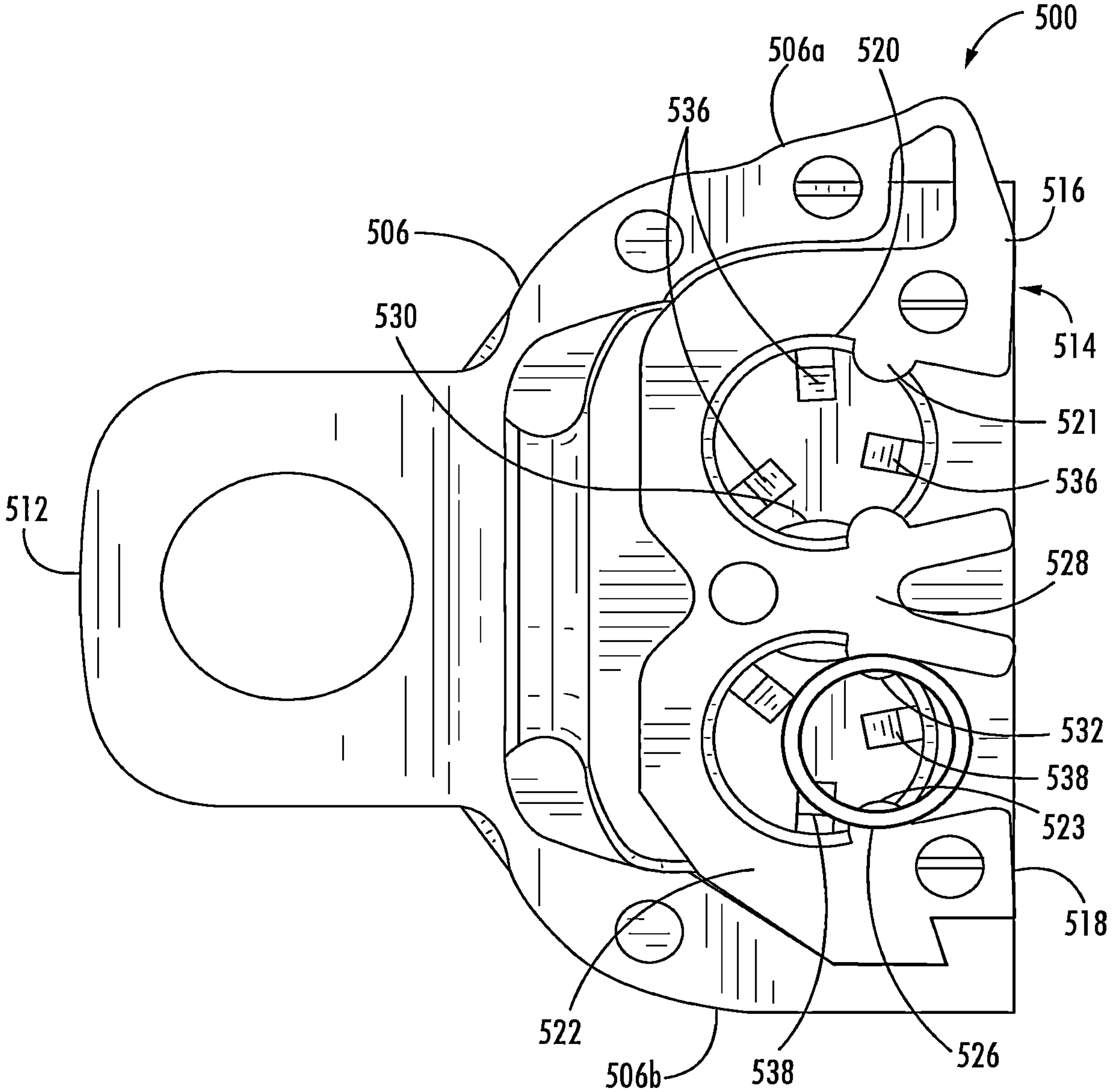
FIG. 19 is a top view of the twin port adapter of FIG. 12, with a feeding tube being inserted therein.

Reference is now made to FIGS. 17 and 18, which show that each of the input ports 508*a*, 508*b* contains a check ball 534*a*, 534*b*, respectively, which constitute and are configured as a check ball valve that acts to block fluid from moving in either direction within the input ports 508*a*, 508*b* and feeding tubes 524, 526. FIG. 17 is a cross-sectional view of the TPA 500 and feeding tubes 524, 526 secured therein, and FIG. 18 is a detailed view of the input ports 508*a*, 508*b* and feeding tubes 524, 526. The check ball 534*a* is supported by three concentrically-arranged ribs 536, while the check ball 534*b* is supported by three concentrically-arranged ribs 538 (see also FIG. 19 in which the check balls 534*a*, 534*b* are removed for clarity). In alternate embodiments, there are different numbers of ribs and/or different rib configurations.

As illustrated in FIG. 18, when both of the check balls 534*a*, 534*b* are in a first, low position, fluid flows from the highest fluid source container (i.e., connected to one of the feeding tubes 524, 526) to the lowest fluid source container due to gravity (as shown by Arrow F). When this occurs in either flow direction (i.e., upstream or downstream within the feeding tubes 524, 526), the check ball 534*a* or 534*b* in the direction of flow will pop up to prevent fluid in the feeding tube 524 or 526 from flowing further (see Arrows $B_1$, $B_2$ and $B_3$, which illustrate the motion of the check balls 534*b*). The ribs 538 also allow the fluid to flow in a forward/downstream flow direction (see Arrows $B_1$ and $B_2$). The check ball 534*a* pushes off the support ribs 536 due to backflow-directed pressure (see Arrow $B_3$) and blocks flow into the feeding tube 524. The blocking action of the check balls 534*a*, 534*b* keep water and food separated until a user is ready to pump same through the feeding pump system. The check balls 543*a*, 534*b* thereby block reverse flow when one of the tubes 524 or 526 has higher pressure than the other in either flow direction.

In various embodiments, the check balls 534*a*, 534*b* are formed from polyethylene. In other embodiments, the check balls 534*a*, 534*b* may be formed from other materials, non-limiting examples of which include polypropylene and polystyrene.

In operation, the feeding tubes 524, 526 are secured within the TPA 500, as described above. The TPA 500 (with the feeding tubes 524, 526 therein) is then coupled to an eccentric bearing pinching mechanism, the same as or similar to the exemplary pinching mechanisms shown in FIGS. 7, 10A-10C and 11A-11D and discussed above. The TPA 500 is installed onto the pinching mechanism having an eccentric bearing (see eccentric bearing 150 in FIG. 7). During installation of the TPA 500, the eccentric bearing is oriented in the central (neutral) position to accommodate the TPA 500. After installation, the eccentric bearing is rotated 90 degrees to the left or right with sufficient force to pinch and stop fluid flow through the first/left feeding tube 524 or second/right feeding tube 526, respectively, as discussed above and shown in shown in FIGS. 10A-10C and 11A-11D.

In preferred embodiments, the TPA 500 is disposable.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, examples, etc., described herein and as such can vary. The terminology used herein is for the purpose of describing particular embodiments only, and is not intended to limit the scope of the present invention, which is defined solely by the claims.

Other terms are defined herein within the description of the various aspects of the invention.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain using no more than routine experimentation, many equivalents to the specific embodiments described herein. Such equivalents are intended to be encompassed by the following claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A valve assembly for an enteral feeding pump system, comprising:

a twin port adapter having first and second feeding tubes, the twin port adapter having a body, including first and second input ports each configured to receive a portion of the first and second feeding tubes therein, respectively; and an output port in communication with the first and second input ports; and a feeding tube guide rotatably connected to the body and configured to secure the first and second feeding tubes within the body;

wherein a portion of the body of the twin port adapter is U-shaped and includes a lower end having first and second sides, and an upper end having first and second sides, and wherein the feeding tube guide is rotatably attached to the first side of the upper end;

the twin port adapter configured to position the first and second input ports in relation with a receiver, the receiver having a central shaft with an eccentric bearing such that at least a portion of the central shaft is received by and within the twin port adapter, the receiver configured to receive the twin port adapter with the central shaft positioned between the first and second input ports while the eccentric bearing is in a first position in which neither of the first and second input ports is compressed; and wherein the eccentric bearing is moveable between the first position, a second position rotated 90 degrees clockwise from the first position in which the eccentric bearing compresses the first input port therein to prevent flow therethrough, and wherein the eccentric bearing is configured to be actuated by a motor within the enteral feeding pump system.

2. The valve assembly of claim 1, wherein the feeding tube guide includes first and second ends, and first and second C-shaped tube-receiving members positioned between the first and second ends and configured to receive and secure the first and second feeding tubes therein, respectively.

3. The valve assembly of claim 2, wherein the first C-shaped tube receiving member includes a first protrusion configured to engage the first feeding tube, and wherein the second C-shaped tube-receiving member includes a second protrusion configured to engage the second feeding tube.

4. The valve assembly of claim 3, wherein the feeding tube guide includes a central wall common to the first and second C-shaped tube-receiving members.

5. The valve assembly of claim 4, wherein the central wall is Y-shaped.

6. The valve assembly of claim 4, wherein the central wall includes a third protrusion opposite the first protrusion and configured to engage the first feeding tube, and a fourth protrusion opposite the second protrusion and configured to engage the second feeding tube.

7. The valve assembly of claim 1, wherein the feeding tube guide is rotatably attached to the first side of the upper end of the body by a living hinge, where the feeding tube guide is moveable from an opened position to a closed position and engages the second side of the upper end to secure the first and second feeding tubes.

8. The valve assembly of claim 1, wherein the portions of the first and second feeding tubes are bonded to the first and second input ports, respectively, with an adhesive.

9. The valve assembly of claim 8, wherein the adhesive is a UV-cured adhesive.

10. The valve assembly of claim 1, further comprising a first check ball proximate the first input port, and a second check ball proximate the second input port, wherein the first and second check balls are configured as a check ball valve that acts to block fluid from moving in either direction within the first and second input ports and feeding tubes.

11. The valve assembly of claim 1, wherein the twin port adapter is disposable.

12. A disposable adapter for use in an enteral feeding pump system having first and second tubes, the disposable adapter comprising:

a body, including:

a U-shaped portion having a lower end with first and second sides and an upper end with first and second sides, the first side and the second side of the upper end being disposed opposite each other along a lateral direction, first and second input ports formed in the lower end and each configured to receive a portion of the first and second tubes therein, respectively;

an output port in communication with the first and second input ports; and a tube guide having a first end rotatably connected to the first side of the upper end and a second end wherein the second end is configured to engage the second side of the upper end upon rotation of the tube guide to a closed position to secure the first and second tubes within the body.

13. The disposable adapter of claim 12, wherein the tube guide is rotatably attached to the first side of the upper end of the body by a living hinge, whereby the tube guide is moveable from an opened position to the closed position.

14. The disposable adapter of claim 12, wherein the tube guide includes first and second C-shaped tube-receiving members positioned between the first and second ends and configured to receive and secure the first and second tubes therein, respectively.

15. The disposable adapter of claim 14, wherein the first C-shaped tube-receiving member includes a first protrusion configured to engage the first tube, and wherein the second C-shaped tube-receiving member includes a second protrusion configured to engage the second tube.

16. The disposable adapter of claim 15, wherein the tube guide includes a central wall common to the first and second C-shaped tube-receiving members.

17. The disposable adapter of claim 16, wherein the central wall is Y-shaped.

18. The disposable adapter of claim 17, wherein the central wall includes a third protrusion opposite the first protrusion and configured to engage the first tube, and a fourth protrusion opposite the second protrusion and configured to engage the second tube.

19. The disposable adapter of claim 12, further comprising a first check ball proximate the first input port, and a second check ball proximate the second input port, wherein the first and second check balls are configured as a check ball valve that acts to block fluid from moving in either direction within the first and second input ports and tubes.

20. The adapter of claim 12, wherein adapter is configured to position the first and second input ports in relation with a receiver, the receiver having a central shaft with an eccentric bearing such that at least a portion of the central shaft is received by and within the disposable adapter, the receiver configured to receive the disposable adapter with the central shaft positioned between the first and second input ports while the eccentric bearing is in a first position in which neither of the first and second input ports is compressed; and wherein the eccentric bearing is moveable between the first position, a second position rotated 90 degrees clockwise from the first position in which the eccentric bearing compresses the first input port therein to prevent flow therethrough, and a third position rotated 90 degrees counterclockwise from the first position in which the eccentric bearing compresses the second input port therein to prevent flow therethrough.

21. An adapter for use with first and second tubes, the adapter comprising:

a body, including:

a U-shaped portion having a lower end with first and second sides and an upper end with first and second sides, the first side and the second side of the upper end being disposed along a lateral direction, first and second input ports formed in the lower end and each configured to receive a portion of the first and second tubes therein, respectively;

an output port in communication with the first and second input ports; and a tube guide rotatably connected to the first side of the upper end, and configured to secure the first and second tubes within the body, the tube guide including first and second ends, and first and second C-shaped tube-receiving members positioned between the first and second ends and configured to receive and secure the first and second tubes therein, respectively;

wherein the second end is configured to engage the second side of the upper end upon rotation of the tube guide to a closed position;

wherein the first C-shaped tube-receiving member includes a first protrusion configured to engage the first tube;

wherein the second C-shaped tube-receiving member includes a second protrusion configured to engage the second tube; and wherein the tube guide includes a central wall common to the first and second C-shaped tube-receiving members and the central wall includes a third protrusion opposite the first protrusion and configured to engage the first tube, and a fourth protrusion opposite the second protrusion and configured to engage the second tube.

22. The adapter of claim 21, wherein the adapter is disposable.

* * * * *